United States Patent [19]
Becker et al.

[11] Patent Number: 5,755,812
[45] Date of Patent: May 26, 1998

[54] BELOW-KNEE PROSTHESIS HAVING AN ADAPTER DISPLACEABLE ON A SPHERICAL SEGMENT SURFACE

[75] Inventors: Karl Becker; Christian Hiemisch, both of Duderstadt, Germany; Roland Schaarschuch, Aryd, Switzerland; Harry Zenner, Best, Netherlands

[73] Assignee: Otto Bock Orthopaedische Industrie Besitz-und Verwaltungs-Kommanditgesellschaft, Duderstadt, Germany

[21] Appl. No.: 612,403

[22] Filed: Mar. 7, 1996

[30] Foreign Application Priority Data

Mar. 7, 1995 [DE] Germany ............ 195 07 894.2

[51] Int. Cl.⁶ .................. A61F 2/62; A61F 2/80
[52] U.S. Cl. ............................. 623/33; 623/38
[58] Field of Search .................. 673/38, 35, 52, 673/50, 53, 55, 36, 37, 39–42, 43, 44–46, 33

[56] References Cited

U.S. PATENT DOCUMENTS

| | | |
|---|---|---|
| 3,422,462 | 1/1969 | Finnieston . |
| 3,928,873 | 12/1975 | Zevering ............ 623/44 |
| 5,013,325 | 5/1991 | Rennerfelt ......... 623/38 |

FOREIGN PATENT DOCUMENTS

| | | | |
|---|---|---|---|
| 0 267 347 | 5/1988 | European Pat. Off. . | |
| 145982 | 1/1962 | Russian Federation | 623/43 |
| 0214096 | 4/1924 | United Kingdom | 623/38 |
| 1161666 | 8/1969 | United Kingdom | 623/38 |
| 2114447 | 8/1983 | United Kingdom | 623/38 |
| 2162069 | 1/1986 | United Kingdom | 623/38 |
| 2169207 | 7/1986 | United Kingdom | 623/38 |
| 9115169 | 10/1991 | WIPO | 623/38 |
| 93/17640 | 9/1993 | WIPO . | |

OTHER PUBLICATIONS

Aqua–Dry brochure.

*Primary Examiner*—David R. Willse
*Attorney, Agent, or Firm*—Foley & Lardner

[57] ABSTRACT

A below-knee prosthesis in which an adapter is displaceable and fixable in relation to the lower socket end on a circular segment surface whose circular arc lies in the sagittal and frontal plane and whose midpoint is the center of the knee.

12 Claims, 2 Drawing Sheets

5,755,812

BELOW-KNEE PROSTHESIS HAVING AN ADAPTER DISPLACEABLE ON A SPHERICAL SEGMENT SURFACE

BACKGROUND OF THE INVENTION

The invention relates to a below-knee prosthesis having a below-knee funnel or socket, receiving the below-knee stump, and a tubular extension piece which are connected to each other via an adapter fastened at the lower end of the below-knee socket.

SUMMARY OF THE INVENTION

The invention is based on the object of developing a below-knee prosthesis which can also be constructed and fitted by less qualified technicians.

According to the invention, this object is achieved by the fact that the adapter is displaceable and fixable in relation to the lower socket end on a circular segment surface whose circular arc lies in the sagittal and frontal plane, and whose midpoint is the center of the knee.

According to the invention, the below-knee prosthesis comprises a below-knee socket for receiving a below-knee stump, and a tubular extension piece having an upper end and a lower end, the upper end being connected to the below-knee socket via an adapter fastened at the lower end of the below-knee socket. The lower end of the tubular extension piece is connected to a matching foot part. The adapter is displaceable and fixable in relation to the lower socket end on a spherical segment surface whose circular arcs—defined by two orthogonal sectional planes—lie in the sagittal and frontal plane. The central point of the ball defining the spherical segment surface is the center of the knee, and the spherical segment surface is the only adjusting surface for the adapter.

By means of the adapter adjustment according to the invention, it is possible to effect a simple and quick correction in terms of flexion and extension, and adduction and abduction.

Even in the event of a change in the position below the shaft in terms of flexion, extension, abduction and adduction, the relationship in the middle to the position of the prosthetic foot never alters. Thus, less qualified technicians can also carry out positional changes without producing serious construction errors, only the below-knee shaft is adjusted in relation to the normal position if correction is required as a result of an unusual stump position. No readjustment need therefore be made to the lower structure of the prosthesis.

So that only a small number of components need be stored for different prosthesis sizes, a complete kit for production of below-knee prostheses may include, for example, only three below-knee sockets of different sizes, which sockets are in each case designed so that the longest possible stump in the respective size range fits it. The different stump lengths which still occur within the three size ranges can be compensated for by inserting one or more supporting pads in the below-knee socket. A different stump circumference is compensated for by adjusting the shell-like below-knee socket with the aid of a clamp device. A different leg length can be accommodated in a simple manner on the spot by adjusting the length of the shaft pipe present in the structure.

In accordance with the invention, a below-knee prosthesis comprises a below-knee socket for receiving a below-knee stump, and a tubular extension piece which is connected to the below-knee socket via an adapter fastened at the lower end of the below-knee socket. The adapter is displaceable and fixable in relation to the lower socket end on a circular segment surface whose circular arc lies in the sagittal and frontal plane, and whose midpoint is the center of the knee.

A cosmetic shaped ankle part is preferably also provided, which ankle part with its upper end engages in a sliding manner over the lower end of the below-knee socket and at its lower end has an annular sealing lip for splash-proof connection to a matching foot part.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred exemplary embodiment of the invention, and, together with the general description given above and the detailed description of the preferred embodiment given below, serve to explain the principles of the invention.

Figure 1:
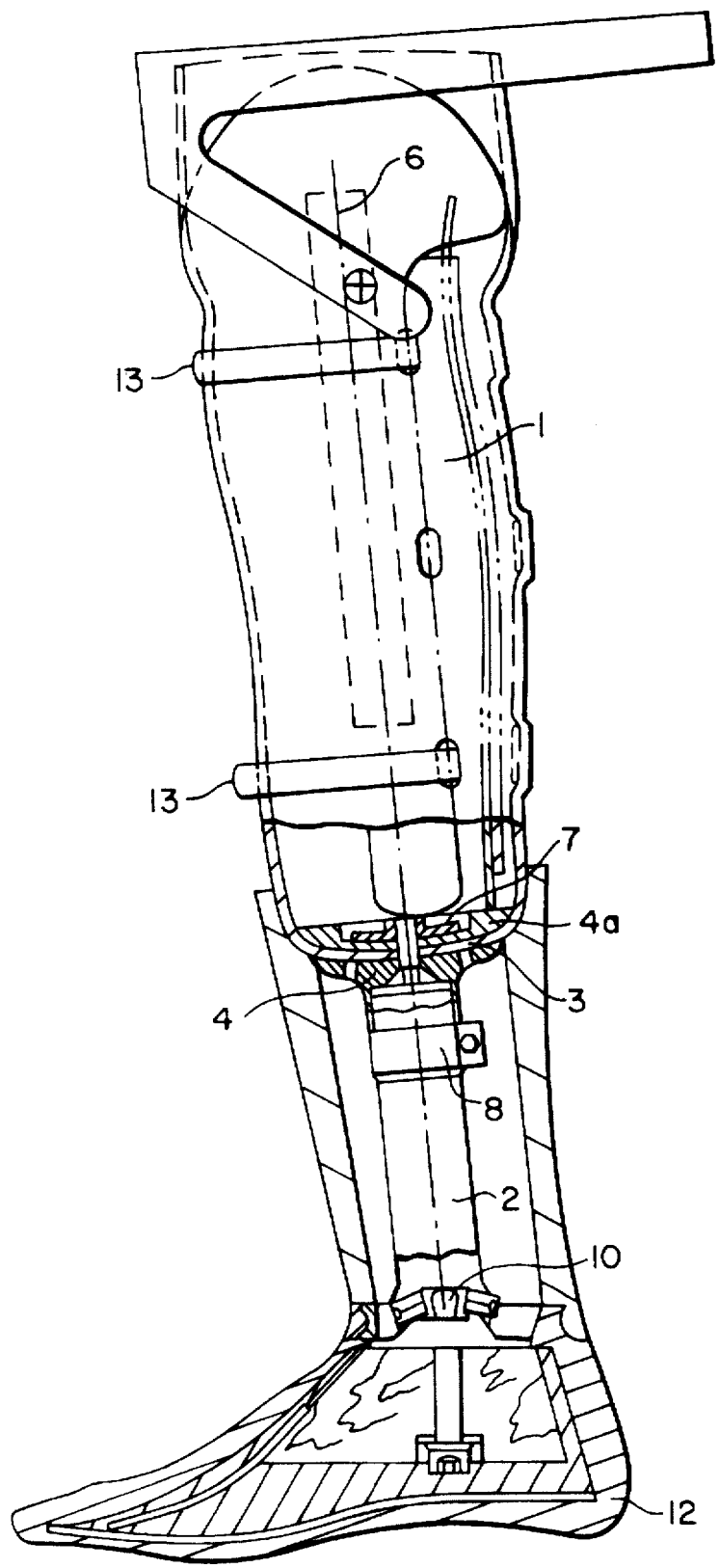
FIG. 1 shows a below-knee prosthesis in a side view, and partly in longitudinal section.
Figure 2:
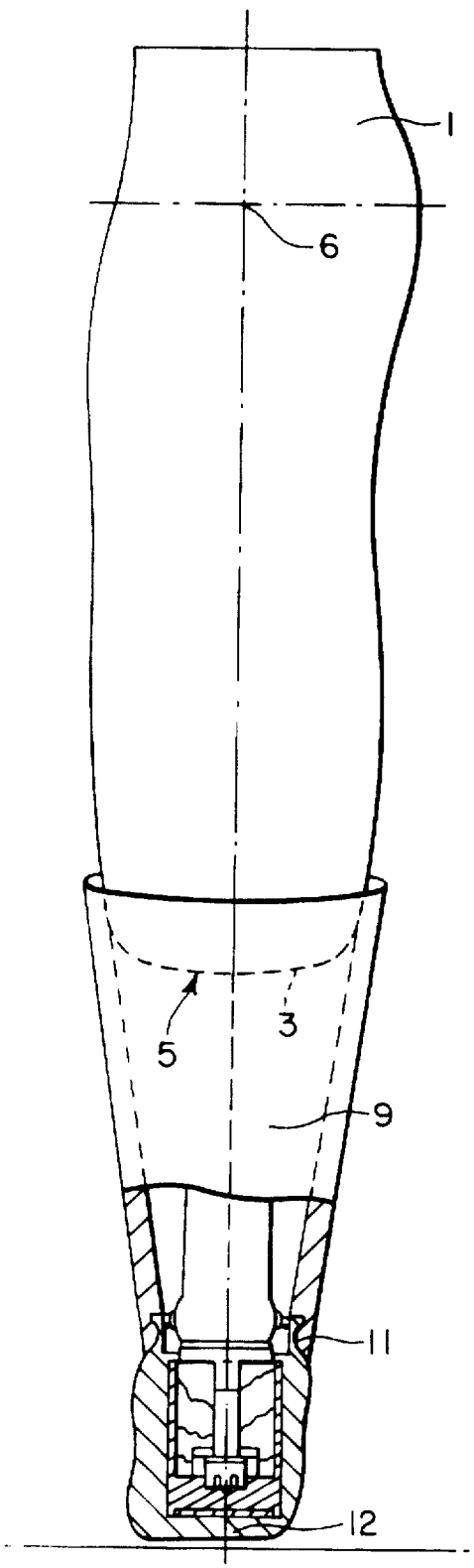
FIG. 2 shows the representation according to FIG. 1 in a rear view.

A below-knee prosthesis is represented in FIGS. 1 and 2, having a below-knee socket 1, receiving the below-knee stump, and a tubular extension piece 2 which are connected to each other via an adapter 4 fastened at the lower end 3 of the below-knee socket 1.

The adapter 4 is displaceable and fixable in relation to the lower socket end 3 on a circular segment surface 5 whose circular arc lies in the sagittal and frontal plane, and whose midpoint 6 is the center of the knee.

The adapter 4 is allocated, inside the lower socket end 3, a correspondingly shaped adapter shell 4a, which is acted upon from above by a clamping screw or clamping disk 7.

The tubular extension piece 2 is fastened in a rotationally adjustable manner on the adapter 4 via a clamping ring 8.

As shown in FIG. 2, also provided is a cosmetic shaped ankle part 9 which with its upper end engages in a sliding manner over the lower end 3 of the below-knee socket 1 and at its lower end has an annular sealing lip 11 for splash-proof connection to a matching foot part 12. The latter is fastened releasably on the lower end of the tubular extension piece 2 via a pyramid-shaped adapter 10.

A different stump circumference is compensated for by adjusting the shell-like below-knee socket 1 with the aid of a clamp device 13.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

We claim:

1. A below-knee prosthesis comprising:
   a below-knee socket for receiving a below-knee stump, and
   an extension piece which is connected to the below-knee socket via an adapter fastened at a lower end of the below-knee socket, wherein the adapter is displaceable and fixable in relation to the lower end of the socket on a spherical segment surface having circular arcs lying in sagittal and frontal planes, and wherein the socket is sized and shaped to engage a residual stump such that a resultant center of a patient's knee coincides with a center defined by said spherical segment surface.

2. The below-knee prosthesis according to claim 1, further comprising an adapter shell, shaped correspondingly to the adapter and located inside the lower end of the socket, which adapter shell is clamped against the lower end of the socket and the adapter by a clamping disk.

3. The below-knee prosthesis according to claim 2, characterized in that the extension piece is fastened in a rotationally adjustable manner on the adapter via a clamping ring.

4. The below-knee prosthesis according to claim 3, further comprising a cosmetic shaped ankle part having an upper end which engages in a sliding manner over the lower end of the below-knee socket and having a lower end which has an annular sealing lip for splash-proof connection to a matching foot part.

5. The below-knee prosthesis according to claim 2, further comprising a cosmetic shaped ankle part having an upper end which engages in a sliding manner over the lower end of the below-knee socket and having a lower end which has an annular sealing lip for splash-proof connection to a matching foot part.

6. The below-knee prosthesis according to claim 1, characterized in that the extension piece is fastened in a rotationally adjustable manner on the adapter via a clamping ring.

7. The below-knee prosthesis according to claim 6, further comprising a cosmetic shaped ankle part having an upper end which engages in a sliding manner over the lower end of the below-knee socket and having a lower end which has an annular sealing lip for splash-proof connection to a matching foot part.

8. The below-knee prosthesis according to claim 1, further comprising a cosmetic shaped ankle part having an upper end which engages in a sliding manner over the lower end of the below-knee socket and having a lower end which has an annular sealing lip for splash-proof connection to a matching foot part.

9. The below-knee prosthesis of claim 1, wherein only the spherical segment surface is an adjusting surface for selectively orienting the adapter relative to the socket.

10. The below-knee prosthesis of claim 1, wherein the extension piece is tubular.

11. A below-knee prosthesis comprising:

a below-knee socket for receiving a below-knee stump, and an extension piece having an upper end and a lower end, the upper end being connected to the socket via an adapter fastened at a lower end of the socket, the lower end of the extension piece being connected to a matching foot part, wherein the adapter is displaceable and fixable in relation to the lower end of the socket on a spherical segment surface having circular arcs—defined by two orthogonal sectional planes—which lie in sagittal and frontal planes, wherein the socket is sized and shaped to engage a residual stump such that a resultant center of a patient's knee coincides with a center defined by said spherical segment surface, and wherein the spherical segment surface is an only adjusting surface for selectively orienting the adapter relative to the socket.

12. The below-knee prosthesis of claim 11, wherein the extension piece is tubular.

* * * * *